United States Patent [19]

Maston et al.

[11] Patent Number: 5,103,818
[45] Date of Patent: Apr. 14, 1992

[54] SYSTEM AND METHOD FOR COMPLETING ELECTRICAL CONNECTIONS IN AN IMPLANTABLE MEDICAL DEVICE

[75] Inventors: Robert E. Maston, Los Gatos; Donald W. Karl, Canyon Country; Alvin H. Weinberg, Moorpark, all of Calif.

[73] Assignee: Siemens-Pacesetter, Inc., Sylmar, Calif.

[21] Appl. No.: 612,358

[22] Filed: Nov. 13, 1990

[51] Int. Cl.⁵ .............................................. A61N 1/375
[52] U.S. Cl. .................................................. 128/419 P
[58] Field of Search ........ 128/419 P, 419 PG, 419 PS

[56] References Cited

U.S. PATENT DOCUMENTS

| | | | |
|---|---|---|---|
| 3,822,707 | 7/1974 | Adducci et al. | 128/419 P |
| 3,884,243 | 5/1975 | Cywinski | 128/419 PS |
| 4,041,956 | 8/1977 | Purdy et al. | 128/419 P |
| 4,127,134 | 11/1978 | Ushakoff | 128/419 P |
| 4,254,775 | 3/1981 | Langer | 128/419 PS |
| 4,262,673 | 4/1981 | Kinney et al. | 128/419 P |
| 4,399,819 | 8/1983 | Cowdery | 128/419 P |
| 4,441,498 | 4/1984 | Nordling | 128/419 P |
| 4,614,194 | 9/1986 | Jones et al. | 128/419 P |
| 4,616,655 | 10/1988 | Weinberg et al. | 128/419 P |

Primary Examiner—William E. Kamm
Attorney, Agent, or Firm—Leslie S. Miller; Albert W. Hilburger

[57] ABSTRACT

An arrangement is provided which enables the rapid and effective termination of electrical junctions for an implantable medical device such as a heart pacemaker, a defibrillator, or a cardioverter. A circuit board supporting electronic circuitry is receivable in a housing for the medical device and is provided with a plurality of female connectors on its outer surface. The female connectors are positioned and shaped to receive and guide mating male components into abutting engagement therewith. The mating male components include feedthrough wires which extend between the interior and the exterior of the housing and conductive pins from a battery used to power the medical device. When the male components and female connectors are in abutting engagement, they are fusion welded as by a laser or electron beam.

13 Claims, 3 Drawing Sheets

SYSTEM AND METHOD FOR COMPLETING ELECTRICAL CONNECTIONS IN AN IMPLANTABLE MEDICAL DEVICE

BACKGROUND OF THE INVENTION

1. Field of the Invention

The present invention relates generally to implantable medical devices and, more particularly, to a system for rapidly and accurately completing sound electrical connections with such devices.

2. Description of the Prior Art

Permanent, implanted cardiac pacemakers can save or lengthen the lives of persons with various cardiac diseases. Today, the principal indications for permanent pacing are complete heart block, intermittent heart block, sick sinus syndrome and other cardiac arrhythmias. The increased use of pacemakers has been paralleled by greater pacemaker reliability and sophistication. Progress in miniaturization of electronic components has made it possible to reliably build smaller, more physiological pacemakers. The initial premise, the use of electrical stimulation to assist the heart, has proven to be a lifesaving and life-enriching idea for pacemaker recipients worldwide.

Because of the great benefits to mankind provided by heart pacemakers and associated electronic implantable medical devices including defibrillators and cardioverters, there is a continuing effort to improve their reliability while reducing their cost so as to make them available to an ever broader range of the population. Currently, the electronic circuitry for implantable medical devices such as a pacemaker is connected to the proximal end of the pacemaker lead via feedthroughs while using flexible interconnect circuitry or discrete wires. The battery is also connected by the same technique. This interconnect scheme generally uses soldering or resistance welding to connect the power source, electronics, and device outputs. It is primarily dependent on operators who typically use a microscope or other magnification device because of the miniaturized components, tweezers, and sophisticated tooling. This operator dependence prevents the use of automation and thereby results in an extremely labor intensive and costly process.

SUMMARY OF THE INVENTION

It was in light of the foregoing that the present invention has been conceived and is now reduced to practice. According to the invention, an arrangement is provided which enables the rapid and effective termination of electrical junctions for an implantable medical device such as a heart pacemaker, a defibrillator, or a cardioverter. A circuit board supporting electronic circuitry is receivable in a housing for the medical device and is provided with a plurality of female connectors on its outer surface. The female connectors are positioned and shaped to receive and guide mating male components into abutting engagement therewith. The mating male components include feedthrough wires which extend between the interior and the exterior of the housing and conductive pins from a battery used to power the medical device. When the male components and female connectors are in abutting engagement, they are fusion welded as by a laser or electron beam.

The solution offered by the present invention is to combine the simple assembly methods provided by pin and socket assembly with the reliability of fusion welding. This enables automatic weld assembly for the connections. Key elements of the connections are located by the parts themselves, minimizing the need for complex tooling or extensive manual involvement by a production operator Geometry and size of these connections are designed specifically to facilitate the introduction of a fusion weld medium to a predetermined location on the connection to weld these connections and form a permanent and reliable connection.

The advantages of this interconnection method include greatly improved and accelerated assembly of device components, increased reliability of these connections due to repeatable and inspectable fusion welding, and the ability to automate the assembly process, specifically by removing the requirement of direct contact of welding electrodes, soldering tips, or other assembly equipment to the areas to be joined. The assembly with this invention can be achieved by "plugging" together the elements to be connected with the mating parts providing the means of relative location. This plugged together assembly can then be fusion welded at predetermined and precise locations by the introduction of a fusion weld medium from a remote source, such as a laser or electron beam.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and, together with the description, serve to explain the principles of the invention in general terms. Like numerals refer to like parts throughout the disclosure.

DESCRIPTION OF THE PREFERRED EMBODIMENTS

Figure 1:
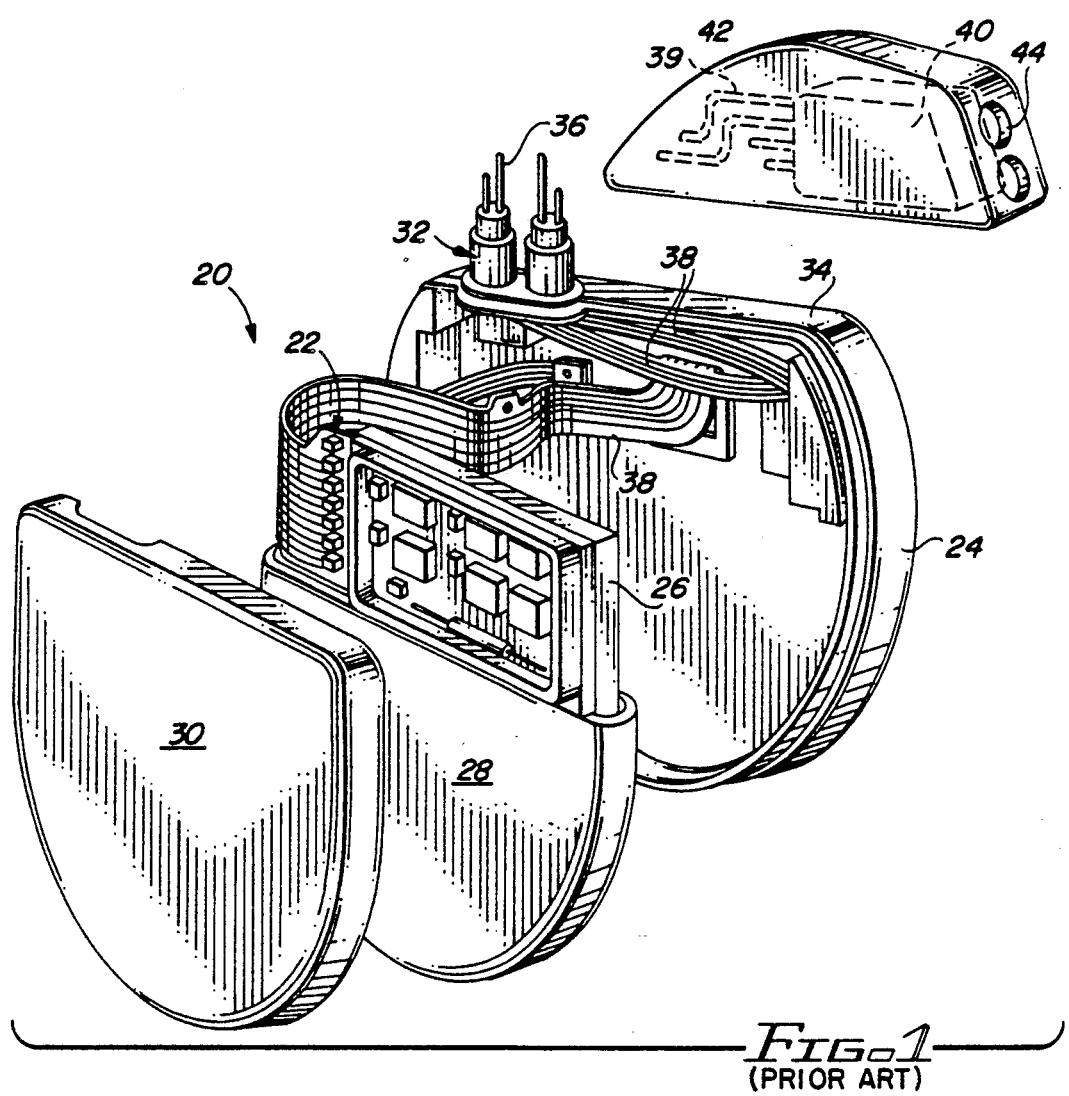
FIG. 1 is a perspective exploded view of a typical prior art implantable medical device, specifically, a heart pacemaker.
Figure 2:
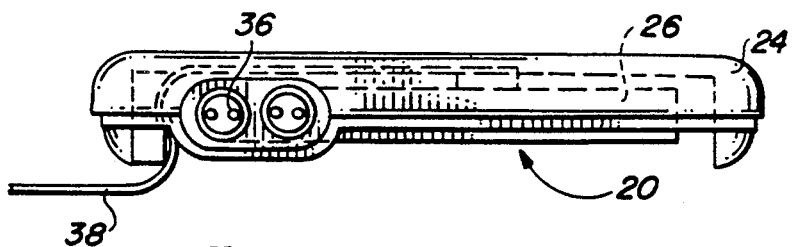
FIGS. 2 and 3 are front elevation and top plan views, respectively, of the implantable medical device illustrated in FIG. 1.
Figure 3:
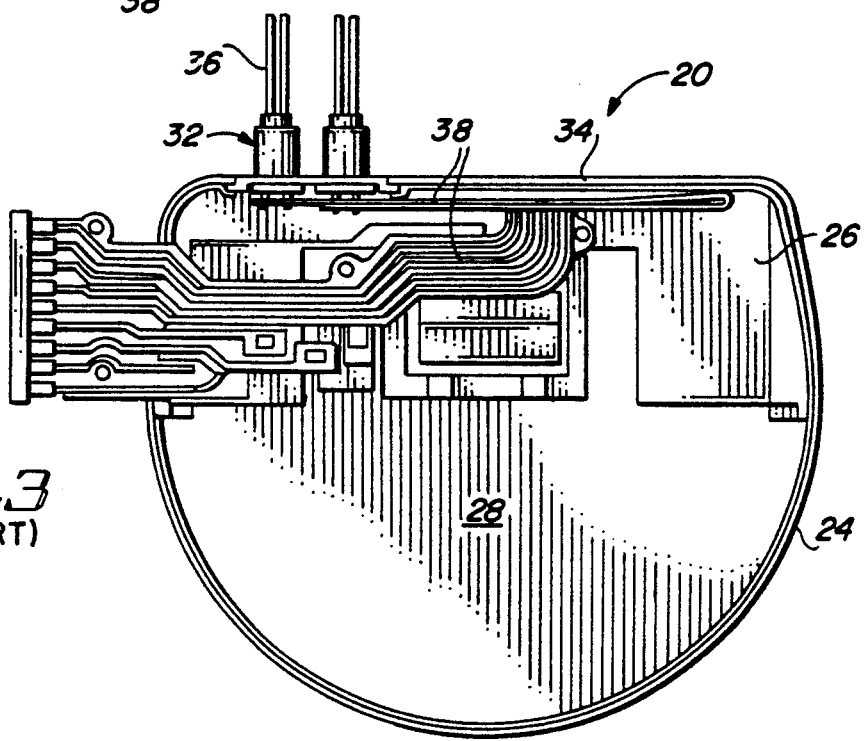

Turn now to the drawings and, initially, to FIGS. 1–5 which illustrate the prior art. More particularly, FIGS. 1–3 illustrate an implantable medical device 20 which is a heart pacemaker although the invention has application to other implantable devices such as defibrillators and cardioverters.

Figure 4:
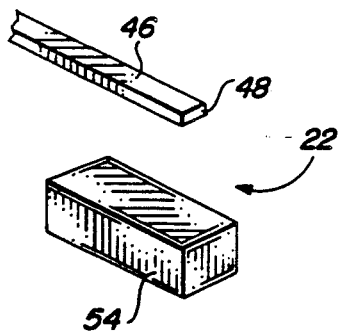
FIG. 4 is a detail perspective view depicting mating components of a prior art connection used in an implantable medical device such as that illustrated in FIG. 1, the components about to be assembled.
Figure 5:
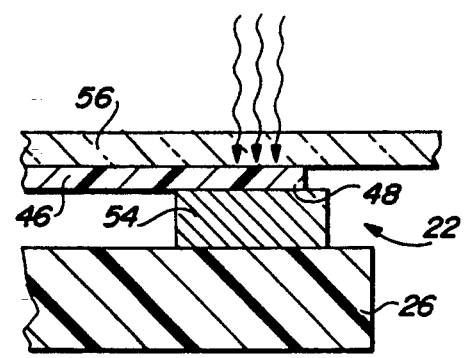
FIG. 5 is a detail side elevation view, in section, illustrating a prior art method of joining the components illustrated in FIG. 4.

FIGS. 4 and 5 are illustrative of conventional electrical connections 22 over which the invention is considered to be a significant improvement.

Returning to FIGS. 1–3, the device 20 is seen to include a housing 24 adapted to receive within its confines a circuit board 26 with suitable electronic circuitry thereon and a suitable battery 28 for energizing the device.

When the circuit board 26 and battery 28 are seated within the housing 24, a cover 30 may be sealingly attached to the housing 24 to insure that all of the components within the housing are fully protected from the surrounding environment.

As seen in FIGS. 1–3, two sets of feedthroughs 32 extend through a sidewall 34 of the housing 24 with adequate insulation to electrically isolate from the housing 24 a pair of feedthrough leads 36. An interior end of each feedthrough lead 36 is suitably joined, as by soldering, to an end of ribbon or flex cable 38 and an opposite end thereof is positioned for engagement with an associated lead 39 to a connector block 40 within a connector top 42 intended for suitable mounting on the sidewall 34 of the housing 24. Proximal ends of pacemaker leads (not shown) are received through suitable jack openings 44 in the connector top 42 for electrical connection with the connector block 40. The distal ends of the pacemaker leads are suitably attached to the heart of the patient.

At its opposite end, the flex cable 38 is attached to the circuit board 26 at a plurality of electrical connections 22 (FIGS. 1, 4, and 5). Each flex cable lead 46 has an end 48 which is to be attached to a metallic pad 54. The metallic pad 54 may be composed of an iron-nickel-cobalt alloy which is suitably mounted on the circuit board 26 (FIG. 5). In a known manner, the end 48 is matingly engaged with the metallic pad 54 as seen in FIG. 5. According to conventional practice, the connection 22 would be completed by means of soldering or by resistance welding. A more recent development has been the use of fusion welding as by laser or electron beams. In the latter instance, as depicted in FIG. 5, a polished quartz plate 56 is positioned so as to overlie the end 48 and the bump 52 to insure that the flex cable lead 46 remains in contact with the metallic pad 54 during the welding process. Then an energy beam 57 is appropriately directed at the junction between the end 48 and the pad 54. When the welding is completed, the quartz plate is removed.

While the connections 22 thereby achieved are satisfactory for their intended purposes, they are difficult to achieve by reason of the inherently unstable (movement-wise) characteristic of the flex cable 38 and its leads 46. To address this situation requires substantial operator effort and is therefore labor intensive, time consuming, and expensive.

The connections 22 serve to connect not only the feedthroughs 32 to the electronic circuitry on the circuit board 26, but also ground wires, battery connections, coil connections, and reed switch leads.

Turn now to FIGS. 6, 7, 8A, and 8B for a description of one embodiment of the invention which serves to overcome the drawbacks of the prior art just described.

Figure 7:
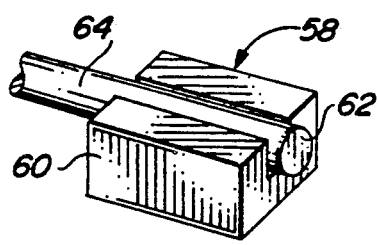
FIG. 7 is a detail perspective view of one embodiment of an electrical connection employed in the implantable medical device illustrated in FIG. 6.

In accordance with the invention, a plurality of female connectors 58 are suitably supported on a circuit board 26A. The circuit board may be composed of a ceramic or other suitable dielectric material. The female connector 58 includes a pad member 60 which may be composed of an alloy of iron, nickel, and cobalt such as that sold under the trademark "KOVAR", or other suitable metal. An undersurface of the pad member 60 is suitably bonded to the circuit board 26a as by brazing, by use of conductive epoxy, or in some other suitable fashion. In any event, the pad member 60 has a longitudinally extending groove 62 which faces in the direction away from the circuit board for mating reception therein of an associated mating male component 64 (FIGS. 7, 8A, and 8B). Each female connector 58 is thus shaped to receive and guide the mating male component 64 into abutting engagement therewith in the groove 62 and thereby achieve electrical continuity with the electronic circuitry provided on the circuit board 26A.

Figure 8C:
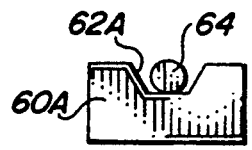
FIG. 8C is a detail end elevation view of an electrical connection somewhat modified from that illustrated in FIG. 8A.
Figure 8A:
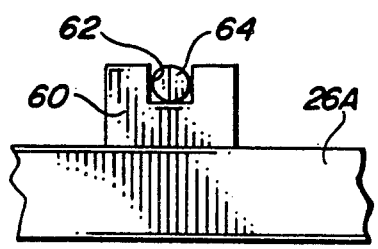
FIG. 8A is a detail end elevation view of the electrical connection illustrated in FIG. 7.
Figure 8B:
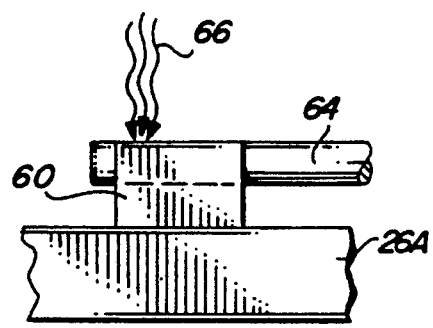
FIG. 8B is a side elevation view of the electrical connection illustrated in FIGS. 7 and 8A and depicting a fusion welding step resulting in a completed connection.

A slightly modified pad member 60A is illustrated in FIG. 8C in which a modified longitudinal groove 62A is provided with sloping walls which further serve to receive and guide the male component 64 into abutting engagement therewith.

When a male component 64 is thus abuttingly engaged within a groove of the pad member 60 or 60A, a beam 66 which may be an electron beam or a laser beam may be directed at the interface between the pad member 60 and the male component 64 as illustrated in FIG. 8B, to thereby fusion weld the male component 64 to the female connector.

Figure 6:
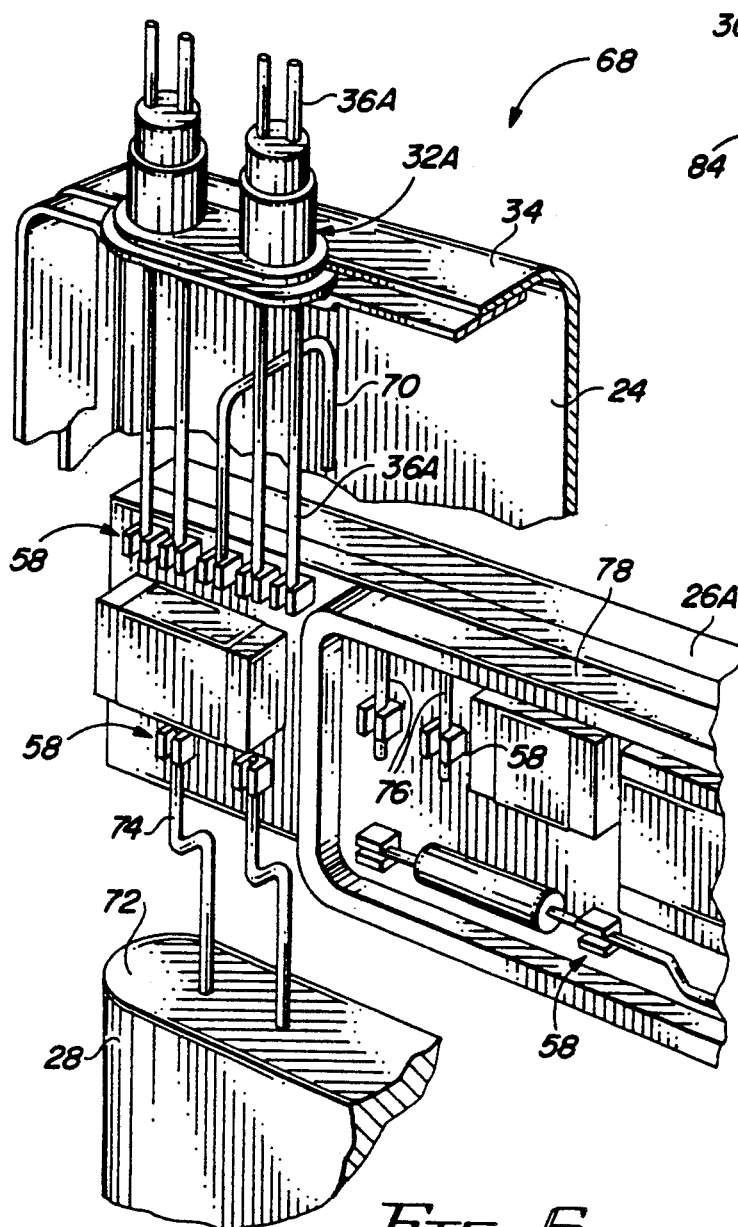
FIG. 6 is a detail perspective view illustrating parts an implantable medical device modified in accordance with the present invention.
Figure 9:
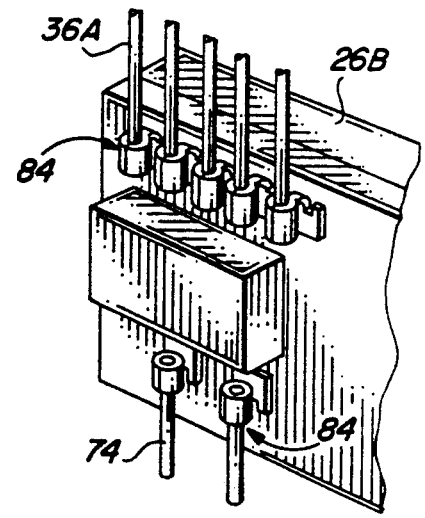
FIG. 9 is a detail perspective view illustrating certain parts shown in FIG. 6 modified to depict another embodiment of electrical connectors used with those parts.
Figure 10:
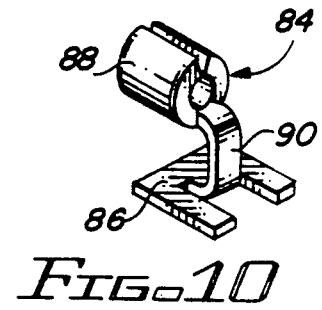
FIG. 10 is a detail perspective view illustrating the embodiment of a female connector of the type depicted in FIG. 9.
Figure 11A:
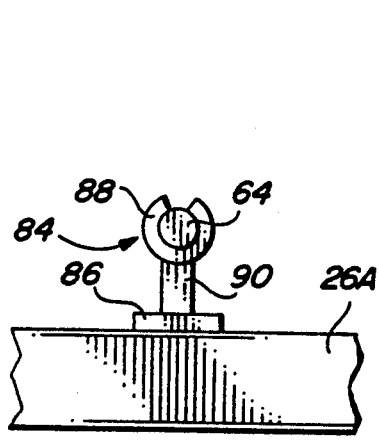
FIG. 11A is an end elevation view of a connection utilizing the connector of FIG. 10.
Figure 11B:
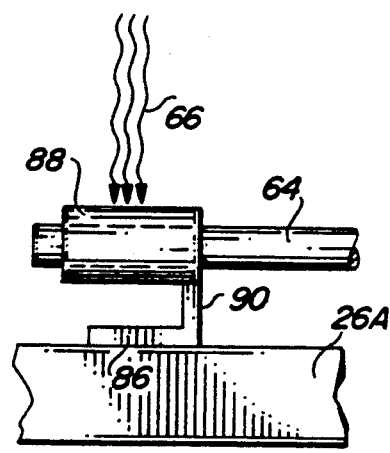
FIG. 11B is a side elevation view of the electrical connection illustrated in FIGS. 10 and 11A and depicting a fusion welding step resulting in a completed connection.

With particular attention to FIG. 6, it will be appreciated that at the time of assembly of an implantable medical device 68, as illustrated, all components are placed in the housing 24 which, in turn, would fit in a suitable locating tool prior to electrical connections being made.

A key feature in the assembly of the device 68, according to the invention, is that the female connectors themselves provide location and orientation relative to their mating components. That is, when the circuit board 26A is placed into the housing 24, each of the feedthrough leads 36A located within the housing 24 is positioned to overlie the grooves 62 in its associated female connector 58. It will be appreciated that in FIG. 6, the feedthrough leads 36A are shown in an exaggerated manner for purpose of explanation. In a similar fashion, a ground wire 70 which has one end integral with the housing 24 also overlies an associated one of the female connectors 58.

With continued reference to FIG. 6, the battery 28 is seen to have an end wall 72 from which a pair of conductive pins 74 extend. As in the instance of the feedthrough leads 36A and the ground wire 70, the conductive pins 74 also overlie the circuit board 26A so as to be in registration with associated female connectors 58 when the battery is inserted into the housing 24 for placement therein.

Other important components may also be connected into the electronic circuitry on the circuit board 26A in a similar manner. For example, leads 76 from an electrical coil 78 may be similarly matingly engaged with associated female connectors 58. Leads 80 from a reed switch 82 may be similarly matingly engaged with associated female connectors 58.

The assembly depicted in FIG. 6 is then placed in a weld chamber where all of the interconnections are fusion welded at one time. It follows that since only one component weld step is required, only one weld inspection step is required. After weld inspection, a cover which may similar to the cover 30 described with respect to the device 20 may be placed onto the housing 24 and sealed.

Another embodiment of the invention is illustrated in FIGS. 9, 10, 11A, and 11B. In this instance, a modified female connector 84 is provided and would be mounted on a circuit board 26B in the same manner as the female connector 58. The female connector 84 includes a foot member 86 for mounting on the circuit board, a tubular split socket 88 for resiliently receiving and gripping an associated mating male component 64. A primary benefit of the female connector 84 is that it provides vibration isolation between the circuit board 26B and the components connected thereto as a protection against jarring movements to which the device 68 may be subject.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. A system for completing electrical connections in an implantable medical device comprising:
   a housing including a sidewall;
   a circuit board supporting electronic circuitry receivable in said housing, said circuit board including a plurality of female connectors thereon, each of said female connectors shaped to receive and guide a mating male component into abutting engagement therewith and each of said female connectors having electrical continuity with said electronic circuitry;
   a battery including a casing having an end wall, said battery adapted for placement in said housing adjacent said circuit board and including a pair of conductive pins projecting away from said endwall so as to overlie said circuit board, each of said conductive pins being matingly engageable with an associated one of said female connectors as said battery is inserted into said housing for placement therein;
   at least a pair of feedthrough wires extending through said sidewall from a location external of said housing to a location within said housing and overlying said circuit board, each of said feedthrough wires being matingly engageable with an associated one of said female connectors;
   said conductive pins being fusion welded to said associated female connectors for mechanical fixation thereto and for electrical continuity between said battery and said electronic circuitry;
   said feedthrough wires within said housing being fusion welded to said associated female connectors for mechanical fixation thereto and for electrical continuity between said feedthrough wires and said electronic circuitry.

2. A system as set forth in claim 1, wherein said implantable medical device is alternatively a heart pacemaker, a defibrillator, or a cardioverter.

3. A system as set forth in claim 1, wherein each of said female connectors includes a pad member and means for fixing said pad member to said circuit board, said pad member having a longitudinally extending groove facing in a direction away from said circuit board for mating reception therein of said associated mating male component.

4. A system as set forth in claim 3, wherein said circuit board includes a substrate composed of a ceramic material;
   wherein said pad member is composed of an alloy of iron, nickel, and cobalt; and
   wherein said pad member has one surface bonded to said substrate and has an opposite surface with said longitudinally extending groove therein.

5. A system as set forth in claim 1, wherein each of said female connectors includes:
   a foot member for mounting on said circuit board;
   a connector member spaced from said foot member for reception therein of said mating male component; and
   strain relief means resiliently joining said connector member to said foot member to thereby isolate said connector member and said mating male component when united from abrupt movements imparted to said circuit board.

6. A system as set forth in claim 5, wherein said connector member includes a tubular split socket for resiliently receiving and gripping an associated said mating male component; and
   wherein said strain relief means includes a pylon integral with said foot member and said socket and transverse thereto, said pylon holding said socket spaced from said foot member.

7. A system as set forth in claim 6, wherein said circuit board includes a substrate composed of a ceramic material; and
   wherein each of said female connectors is composed of nickel.

8. A system as set forth in claim 1, wherein said circuit board has supported thereon an electrical coil having a pair of male coil leads extending from said electrical coil, said male coil leads being matingly engageable with an associated one of said female connectors, said male coil leads being fusion welded to said associated female connectors for mechanical fixation thereto and for electrical continuity between said electrical coil and said electronic circuitry.

9. A system as set forth in claim 1 including:
   a reed switch having input and output leads extending therefrom; and
   wherein said circuit board has supported thereon a pair of female connectors positioned and shaped for guiding reception of said switch leads into abutting engagement therewith, said switch leads being fusion welded to said associated female connectors for mechanical fixation thereto and for electrical continuity between said reed switch and said electronic circuitry.

10. A system for completing electrical connections in an implantable medical device comprising:

a housing including a planar bottom wall;

a circuit board supporting electronic circuitry thereon receivable in said housing so as to lie in a plane parallel to said bottom wall, said circuit board including a plurality of female connectors thereon, each of said female connectors shaped to receive and guide a mating male component into abutting engagement therewith generally lying within a plane parallel to said bottom wall, each of said female connectors having electrical continuity with said electronic circuitry;

each of said mating male components being fusion welded to said associated female connectors for mechanical fixation thereto and for electrical continuity between each of said male components and said electronic circuitry.

11. A method of completing electrical connections within an implantable medical device comprising the steps of:

providing a circuit board supporting thereon electronic circuitry and a plurality of female connectors having electrical continuity with said electronic circuitry, each of the female connectors being shaped to receive and guide a mating male component into abutting engagement therewith;

assembling the circuit board and a battery for energizing the electronic circuitry, the battery including outwardly projecting conductive pins, in the interior of a housing having at least a pair of feedthrough wires extending to a location within the housing, such that each of the feedthrough wires is matingly engaged with an associated one of the female connectors and such that each of the conductive pins is matingly engaged with an associated one of the female connectors; and fusion welding in a single operation all of the matingly engaged male components and their associated female connectors.

12. A method as set forth in claim 11 including the step of isolating the female connectors and their associated united mating male components from abrupt movements imparted to the circuit board.

13. A method as set forth in claim 11, wherein the isolating step includes the step of resiliently mounting the female connectors on the circuit board.

* * * * *